United States Patent [19]
Grabover et al.

[11] Patent Number: 5,938,588
[45] Date of Patent: Aug. 17, 1999

[54] SUPERELASTIC CONTROL WIRE SHEATH FOR FLEXIBLE ENDOSCOPE

[75] Inventors: Edward A. Grabover, Danbury; Gregory S. Konstorum, Stamford, both of Conn.

[73] Assignee: Circon Corporation, Goleta, Calif.

[21] Appl. No.: 08/882,592

[22] Filed: Jun. 25, 1997

[51] Int. Cl.⁶ ..................................................... A61B 5/04
[52] U.S. Cl. ........................... 600/150; 600/143; 600/149
[58] Field of Search .................................. 600/139, 141, 600/142, 143, 146, 149, 150, 585; 604/280, 281

[56] References Cited

U.S. PATENT DOCUMENTS

| | | | |
|---|---|---|---|
| 3,162,214 | 12/1964 | Bazinet, Jr. | 138/120 |
| 3,572,325 | 3/1971 | Bazell et al. | 600/141 |
| 4,580,551 | 4/1986 | Siegmund et al. | 128/4 |

*Primary Examiner*—Jeffrey A. Smith
*Assistant Examiner*—Ira Hatton
*Attorney, Agent, or Firm*—Perman & Green, LLP

[57] ABSTRACT

An endoscope comprising a handle and a flexible shaft connected to the handle. The flexible shaft has an active deflection section and a passive deflection section with a control wire support member therein. The endoscope also has a control wire connected to the active deflection section. A portion of the control wire is housed in the control wire support member. The control wire support member is made from a superelastic alloy material and is resiliently deflectable bending with the passive deflection section without permanent deformation or substantial fatigue over a working life of the endoscope.

17 Claims, 1 Drawing Sheet

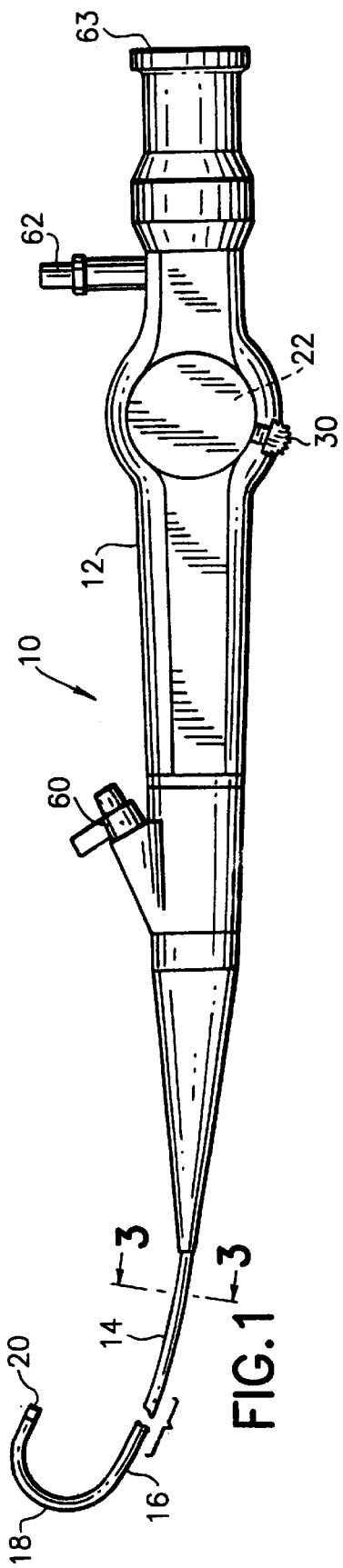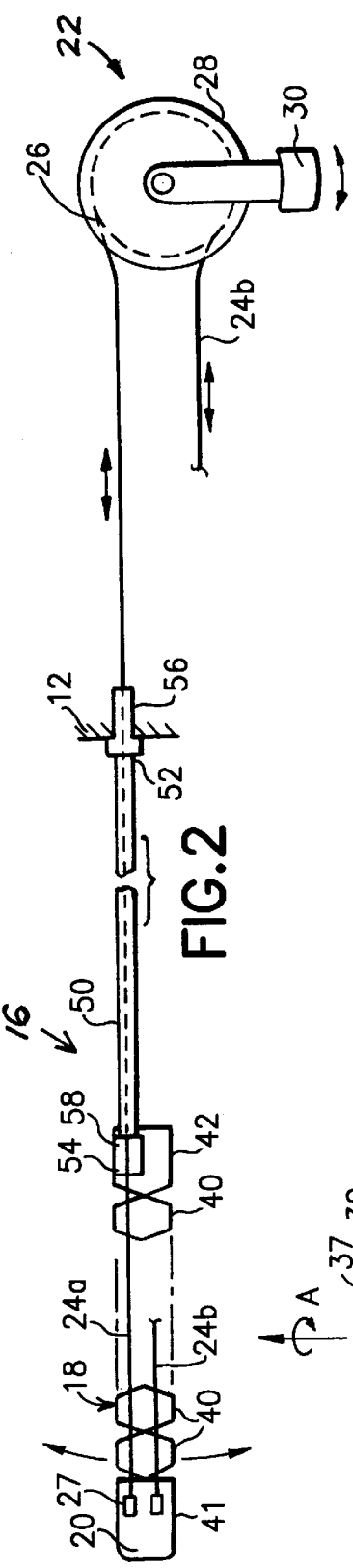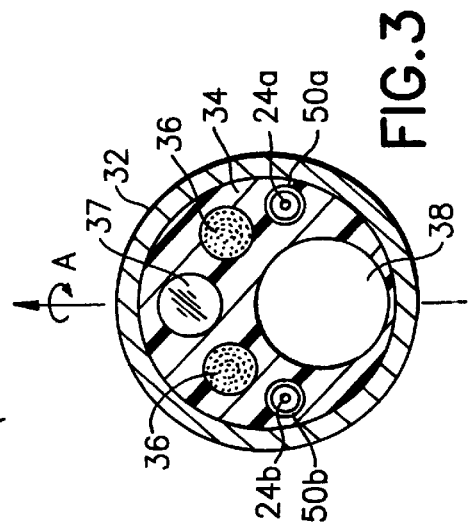

SUPERELASTIC CONTROL WIRE SHEATH FOR FLEXIBLE ENDOSCOPE

BACKGROUND OF THE INVENTION

1. Field of the Invention

The present invention relates to medical instruments and, more particularly, to an endoscope having flexible tubes within a passive deflection section.

2. Prior Art

Endoscopes with passive and active deflection sections are known in the art. U.S. Pat. No. 4,580,551 shows an endoscope with an elongated flexible plastic tube comprising a continuous sequence of connected vertebra-like elements. U.S. Pat. No. 3,162,214 discloses a thin walled tube of elastic material internally supported throughout its length by a series of tubular rigid rings. In one prior art embodiment, control wires from a deflection control to a distal tip of the active deflection are provided with a wire sheath along the passive deflection section. The wire sheath comprises a coiled wire to form a flexible tube around each control wire. A problem exists with these coil wire sheaths in that the coil shape can expand during compression. This can result in a loss of deflection at the active deflection section of the endoscope. In another prior art embodiment, stainless steel tubes are used as the sheaths for the control wires. However, these are only used in applications which have a large bend radius. These tubes can kink very easily, have no resilience, and can fatigue and permanently deform thereby shortening the working life of the endoscope.

SUMMARY OF THE INVENTION

In accordance with one embodiment of the present invention, an endoscope is provided comprising a handle and a flexible shaft connected to the handle. The flexible shaft has an active deflection section and a passive deflection section with a control wire support member therein. The endoscope has means for controlling the active deflection section comprising a control wire connected to the active deflection section. A portion of the control wire is housed in the control wire support member. The control wire support member is made from a superelastic alloy material and is resiliently deflectable, bending with the passive deflection section, without permanent deformation or substantial fatigue over a working life of the endoscope.

In accordance with another embodiment of the present invention, an endoscope is provided having a handle and a flexible shaft connected to the handle. The flexible shaft has a passive deflection section and an active deflection section operated by a control wire. The passive deflection section has a sheath holding a portion of the control wire therein. The sheath is made from a superelastic alloy material and is resiliently deflectable to bend with the passive deflection section without permanent deformation or substantial fatigue over a working life of the endoscope. The sheath has continuous column strength to support axial loads without cross-sectional and longitudinal deformation or loss of flexibility.

In accordance with still another embodiment of the present invention, an endoscope is provided comprising a handle and a flexible shaft connected to the handle. The flexible shaft comprises a passive deflection section adjoining the handle and an active deflection section at a distal end. The endoscope has means for controlling the deflection of the active deflection section comprising control wires connected to the active deflection section. The passive deflection section has wire sheaths attached thereto and a portion of each control wire passes through a corresponding wire sheath. Each of the wire sheaths has a longitudinally constant cross-section. Each of the wire sheaths is made from superelastic alloy material and is resiliently deflectable to bend with the passive deflection section without permanent deformation or fatigue over a working life of the endoscope.

BRIEF DESCRIPTION OF THE DRAWINGS

The foregoing aspects and other features of the invention are explained in the following description, taken in connection with the accompanying drawings, wherein:

FIG. 1 is an elevational side view of an endoscope incorporating features of the present invention;

FIG. 2 is a schematic view of the active deflection section, the control system for the active deflection section, and a control wire sheath of the endoscope shown in FIG. 1; and FIG. 3 is a cross-sectional view of the passive deflection section of the endoscope taken along line 3—3 in FIG. 1.

DETAIL DESCRIPTION OF THE PREFERRED EMBODIMENT

Referring to FIG. 1 there is shown an elevational side view of an endoscope 10 incorporating features of the present invention. Although, the present invention will be described with reference to the single embodiment shown in the drawings, it should be understood that features of the present invention can be embodied in various different forms of alternate embodiments. Features of the present invention can be embodied in various different types of endoscopes. In addition, any suitable size, shape or type of elements or materials could be used.

The endoscope 10 generally comprises a handle 12, a flexible shaft 14 connected to the handle 12, and an active deflection section 18 connected to the distal end of the shaft 14. The flexible shaft 14 includes a passive deflection section 16 adjoining the active deflection section 18. A control system 22 to control the active deflection section 18 extends from the handle 12 to the active deflection section 18 as schematically shown in FIG. 2. Referring also to FIGS. 2 and 3, the control system 22 generally comprises a pair of control wires 24a, 24b, two wire sheaths 50a, 50b, and an actuator 28. The wires 24a, 24b are connected to the actuator 28 at one end 26 and are connected to the active deflection section 18 at a second end 27.

In the preferred embodiment, the handle 12 has a user operated slide or lever 30. The lever 30 is connected to the actuator 28. The actuator 28 is adapted to pull and release the two wires 24a, 24b of the control system 22. When the lever 30 is moved by the user, the actuator 28 is moved. The actuator 28 may be a drum or pulley rotatably connected to the handle 12 to pull one wire 24a, 24b while releasing the other. In an alternate embodiment, the actuator may be of any other type, such as a rocker arm, adapted to pull and release the wires of the control system 22. In another alternate embodiment, where the control system may have two or more pairs of control wires, the handle will have additional actuators and corresponding controls to drive the additional pairs of control wires. In still other alternate embodiments, the handle may have knobs or other suitable user operated controls for the control system.

The flexible shaft 14 is cantilevered from the handle 12. In the preferred embodiment, the flexible shaft 14 has a 7.4 Fr diameter. In alternate embodiments, the flexible shaft could have any suitable diameter. The flexible shaft 14 includes the control wires 24a, 24b of the control system 22, a fiber optic image bundle 37, two fiber optic illumination bundles 36, and a working channel 38, as shown in FIG. 3. A port 60 for inserting instruments (not shown) into the operating channel 38 is located on the handle 12. The handle 12 also has a light source post 62 for connecting a light source (not shown) to the illumination bundles 36. In addition, the handle 12 has an eyepiece 63 for a user to view an image transmitted by the image bundle 37 from the front end 20. In alternate embodiments, the flexible shaft may house different systems within.

The control wires 24a, 24b extend from the actuator 28 through the flexible shaft 14 to the distal end 20 where the wires 24a, 24b are connected to the active deflection section 18. The active deflection section 18 is comprised of a sequence of pivotably connected rigid elements 40. Each rigid element 40 is connected to the adjoining elements 40 in sequence by joint means (not shown), such as pins or resiliently deflectable elements. This enables each element 40 to rotate about the single rotational degree of freedom provided by the joint as indicated by the arrows in FIG. 2. The combined action of the rigid elements 40 allows the active deflection section 18 to be deflected 180° or more. The deflection of the active deflection section 18 is controlled by the pair of wires 24a, 24b of the control system 22. Each wire 24a, 24b passes through the rigid elements 40 and connects to the distal element 41 eccentric to the axis of rotation "A" of the elements 40, as shown in FIGS. 2 and 3. Hence, by pulling one of the wires 24a, 24b and releasing the other, as when operating the actuator 28, the rigid elements 40 are rotated to achieve the requisite deflection of the active deflection section 18 of the flexible shaft 14. Various types of rigid elements and joints linking the elements to form an active deflection section are known in the art, and therefore, the active deflection section is not described further.

The active deflection section 18 is supported from the passive deflection section 16 of the flexible shaft 14. The shaft 14 comprises an outer flexible casing 32. The outer casing 32 covers substantially the entire flexible shaft 14 from the handle 12 to the active deflection section 18. The outer casing 32 is not shown in FIG. 2 for clarity purposes. The outer casing 32 may be made from a closed wound spiral spring with an elastomer cover or any other flexible casing. Within the outer casing 32, the shaft 14 has an elastic core 34 with the wire sheaths 50a, 50b extending therethrough. Each control wire 24a, 24b passes through the shaft 14 within a corresponding wire sheath 50a, 50b. Each wire sheath 50a, 50b, has a generally cylindrical tube shape. The proximal end 52 of each wire sheath 50a, 50b is fixedly connected to the adjustable fitting 56. The distal end 54 of each wire sheath 50a, 50b is fixedly connected to the rear end of the active deflection section 18. Referring specifically to FIG. 2, in the preferred embodiment, each wire sheath 50a, 50b has the adjustable fitting 56 at the proximal end 52 which is slip fit into the handle 12 to connect the respective wire sheath 50a, 50b thereto. At its distal end 54, each wire sheath 50a, 50b has a fitting 58 captured within a complementing recess in the proximal element 42 of the active deflection section 18 forming the connection between each wire sheath 50a, 50b, and the active deflection section 18. The above is merely illustrative of the way each wire sheath 50a, 50b may be connected to the handle 12 and the active deflection section 18 to provide a fixed connection capable of transferring both axial and transverse forces with respect to the longitudinal axis or the respective wire sheaths 50a, 50b. In alternate embodiments, the respective wire sheaths may be connected to the handle and active deflection section by any suitable means, such as adhesive, capable of transferring these forces. In the preferred embodiment, the wire sheaths 50a, 50b, have a substantially straight natural shape. In alternate embodiments, the wire sheaths may have any other longitudinal shape.

The wire sheaths 50a, 50b, are made as solid tubes from a shape memory alloy material, such as Tinel or Nitinol. The shape memory alloy material is used for its superelastic properties exhibited by the material's ability to deflect and resiliently return to its natural or predetermined position even when material strains approach 4.0%, or an order of magnitude greater than the typical yield strain of 0.4% giving rise to plastic deformation in common metals. Thus, the term "superelastic alloy" material is used to denote this material. A benefit provided by the present invention is that by supporting the control wires 24a, 24b in the sheaths 50a, 50b made from superelastic material, the accuracy and total deflection of the active deflection section 18 is enhanced in comparison to endoscopes having control wires housed in closed wound spring wire sheaths. Referring now to FIG. 2, pulling and releasing the control wires 24a, 24b to deflect the active deflection section 18 imposes axial forces on the wire sheaths 50a, 50b. Respectively, these forces attempt to longitudinally compress and expand the wire sheaths 50a, 50b. Longitudinal compression and expansion of the prior art wire sheaths, and the resulting increase or decrease in cross-sections arising from compression or extension of the wire sheaths, had deleterious effects on the accuracy and total deflection of the active deflection section. Two factors contribute to these effects. First, when the prior art wound wire sheaths are longitudinally compressed or extended, part of every movement of the control wires is taken up by that compression or extension of the wire sheath, and hence is not available to deflect the active deflection section. Second, changes in the cross-section in the prior art coil wound wire sheath tend to alter the bend radius and deflection of the wire sheath and of the passive deflection section. The active deflection section is supported by the passive deflection section, and thus, changes in the deflection of the passive deflection section tend to reposition the active deflection section with potentially significant variances at the distal end of the active deflection section. The present invention eliminates these problems because the control wire sheath 50a, 50b, made from the superelastic material are not significantly longitudinally compressible or expandable. Nor is there a substantial increase or decrease in the cross-section of the sheaths 50a, 50b, due to axial forces. When the user operates the lever 30 on the handle 12 to pull and release the control wires 24a, 24b, every movement of the lever 30, and corresponding pull and release of the wires 24a, 24b, has a substantially immediate, direct and precise effect on the deflection of the active deflection section 18. There are substantially no inaccuracies from having a component of every movement of the wires 24a, 24b lost in compressing or expanding the control wire sheaths 50a, 50b. There is substantially no loss in the total deflection of the active deflection section 18. In comparison, wound prior art wire sheaths were longitudinally compressible and expandable. Additionally, the cross-section of these prior art wound wire sheaths increased when the sheaths are compressed and decreases when the sheaths expanded. Consequently, closed wound spring wire sheaths induced inaccuracies and loss of deflection at the active deflection section.

The sheaths 50a, 50b also provide an advantage in regard to their function at the passive deflection section 16. Users use the passive deflection section 16 to contact and push the shaft 14 off of a tissue wall of the patient to get the distal end 20 into a position at a bottom portion inside a kidney. In the prior art, the lateral forces exerted against the wound wire sheaths from this redirection caused them to deform. This resulted in loss of deflection and accuracy at the active deflection section. With the solid tube sheaths 50a, 50b of the present invention, on the other hand, the sheaths can withstand the lateral forces from a redirection by pushing off of a tissue wall without loss of deflection or accuracy at the active deflection section 18. Thus, the use of a solid tube as the control wire sheath added the advantage of withstanding lateral forces without detrimentally effecting deflection at the active deflection section. The passive deflection section 16 can be less stiff than the rest of the shaft 14. In a preferred embodiment, the passive deflection section 16 is about 1 inch to about 1.5 inches long. However, any suitable length could be provided.

The ability of the superelastic alloy material to resiliently deflect to large strain values is also an indication of the superior fatigue resistance possessed by this material, even in comparison to steel spring alloy. Hence, when the flexible shaft 14 of the endoscope 10 is inserted in a ureter (not shown) and the shaft 14 bends to accommodate the shape of the ureter, the wire sheaths 50a, 50b bend with the shaft 14 without permanent deformation of the wire sheaths 50a, 50b. In addition, the passive deflection section 16, and with it the wire sheaths 50a, 50b therein, may be repeatedly bent without significant fatigue of the sheaths 50a, 50b. Frequent bending of the wire sheaths 50a, 50b, over the life of the endoscope 10, which may be counted in decades, will not cause significant loss of resilience or failure of the sheaths 50a, 50b from fatigue. The wire sheaths 50a, 50b also assist the passive deflection section 16 and shaft 14 to maintain its predetermined shape by retaining their natural shape despite repeated bending. For example, after the passive deflection section 16 is bent, the wire sheaths 50a, 50b urge the passive deflection section 16 back to its home position with substantially the same force after every use. Furthermore, the wire sheath 50a, 50b have substantial axial stiffness when in their natural or generally undeflected state which facilitates insertion of the flexible shaft 14 in the ureter. In this state, the wire sheath 50a, 50b, made from the superelastic alloy material retains the relatively high modulus of elasticity of most metal alloys (e.g. 28 msi for steel) This provides substantial rigidity to the sheath 50a, 50b against longitudinally applied loads that occur when inserting the flexible shaft 14 in the ureter. Correspondingly, the column strength of the control wire sheaths 50a, 50b resists premature collapse or bending of the passive deflection section 16 from axial loads, thereby imparting axial stiffness to the passive deflection section 16 of the flexible shaft 14. Even in embodiments where the sheaths and the passive deflections section have a generally curved natural shape the control wire sheaths continue to provide the passive deflection section with significant resistance against axial loads. Thus, when inserting the flexible shaft 14 in the ureter, the user may apply sufficient insertion forces from the handle 12 without collapsing the flexible shaft 14 outside the ureter. In this fashion, the control wire sheaths 50a, 50b facilitate insertion of the flexible shaft 14 in the ureter over the life of the endoscope 10, because the sheaths 50a, 50b do not lose substantial strength or resilience as a result of fatigue.

In comparison, control wire sheaths known in the art are subject to limited resilient deflection and fatigue damage in the case of sheaths made from typical metals with consequent loss of resilience and strength, or poor axial strength and a tendency to kink under compression in the case of sheaths made from elastic materials. Typical metals, including spring steel, start to undergo plastic deformation at generally low strain values of about 0.2%–0.4%. Hence, sheaths of sufficient diameter to house a control wire and with a constant longitudinal cross-section made from these metals have limited resilient deflection which makes such sheaths impractical for use in the flexible shaft of an endoscope. To accommodate the large deflections associated with use in endoscopes, designers made the existing control wire sheaths from closed wound spring wire which dramatically increases the length of the material being deflected allowing large deflections within the low elastic strain limits of spring steel. Nevertheless, large deflections of these sheaths induce strains in the coiled spring wire comparable to the yield strain of the spring steel material. The closer the applied strains approach the material yield strain under repeated bending, the less the tolerance of the material to fatigue damage, which means that the material weakens, losing resilience and ultimately failing after a substantially smaller number of bending and unbending cycles. Thus, control wire sheaths made from coiled spring wire may lose resilience and fail due to fatigue from repeated bending over the life of the endoscope. Loss of resilience from fatigue also means that sheaths made from closed coiled spring wire do not assist the passive deflection section return to its natural shape after being bent repeatedly. Closed wound wire sheaths also suffer from having low column strength, because they lack a continuous longitudinal cross-section. As a result, these sheaths may collapse prematurely under the axial loads applied when the user inserts the flexible shaft in the ureter. Control wire sheaths in the art made from elastic materials are not subject to fatigue or plastic deformation under large deflections. However, they exhibit little axial stiffness due to a small modulus or elasticity. Consequently, these sheaths are also susceptible to kink or collapse prematurely when the user inserts the flexible shaft in the ureter. Sheaths made from stainless steel tubes in the prior art could not bend at small radii, such as inside a patient's kidney. The control wire sheaths 50a, 50b of the present invention overcome these limitation of sheaths known in the art.

The present invention provides an endoscope 10 having a flexible shaft 14 with superelastic alloy sheaths 50a, 50b that are resiliently deflectable and are substantially resistant to fatigue increasing the useful life of the endoscope 10. The sheaths 50a, 50b assist the flexible shaft 14 to retain its natural shape and prevent the shaft's 14 premature collapse during insertion in a ureter, even after repeated use. This improves the insertion capability of the endoscope 10. Finally, the sheaths 50a, 50b improve the accuracy and total deflection the user may obtain when controlling the active deflection section 18 of the flexible shaft 14.

It should be understood that the foregoing description is only illustrative of the invention. Various alternatives and modifications can be devised by those skilled in the art without departing from the scope of the present invention. Accordingly, the present invention is intended to embrace all such alternatives, modifications and variances which fall within the scope of the appended claims.

What is claimed is:

1. An endoscope comprising:
   a handle;
   a flexible shaft connected to the handle, the flexible shaft having an active deflection section and a passive deflection section with a control wire support member therein; and
   means for controlling the active deflection section comprising a control wire connected to the active deflection section, a portion of the control wire being housed in the control wire support member;

wherein the control wire support member is an elongated solid tube made from a superelastic alloy material and is resiliently deflectable, bending with the passive deflection section and returning to its original shape when released whereby the support member experiences minimal permanent deformation or fatigue.

2. An endoscope as in claim 1 wherein the control wire support member has a first end fixedly connected to the handle and a second end anchored to a proximal end of the active deflection section.

3. An endoscope as in claim 1 wherein the control wire support member has a general cylindrical tube shape.

4. An endoscope as in claim 1 wherein the control wire support member has a substantially straight natural shape.

5. An endoscope as in claim 1 wherein the control wire support member retains a predetermined shape so that when the passive deflection section is bent from its natural shape the control wire support member assists the passive deflection section to return to the natural shape.

6. An endoscope as in claim 1 wherein the control wire support member has a longitudinally constant cross-section to support axial loads without substantial cross-sectional or longitudinal deformation.

7. An endoscope as in claim 1 wherein the means for controlling the active deflection section comprises at least two of the control wires connected to the active deflection section.

8. An endoscope as in claim 7 further comprising at least two of the control wire support members corresponding to the control wires, wherein each of the control wires has a portion housed in one of the corresponding control wire support members.

9. In an endoscope having a handle, a flexible shaft connected to the handle, the flexible shaft having a passive deflection section and an active deflection section operated by a control wire, wherein the improvement comprises:

the passive deflection section having a wire sheath being an elongated solid tube made from a super elastic alloy material holding a portion of the control wire therein, the wire sheath being resiliently deflectable to bend with the passive deflection section and return to its original shape when released whereby the wire sheath has continuous column strength to support axial loads with minimal cross-sectional and longitudinal deformation or loss of flexibility.

10. An endoscope as in claim 9 wherein the wire sheath is fixedly connected at a proximal end to the handle by an adjustable fitting and is fixedly connected at a distal end to the active deflection section.

11. An endoscope as in claim 9 wherein the wire sheath has a substantially straight natural shape.

12. An endoscope as in claim 9 wherein the wire sheath retains a predetermined shape so that when the passive deflection section is bent from its natural shape the wire sheath assists the passive deflection section return to its natural shape.

13. An endoscope as in claim 9 wherein the passive deflection section comprises a plurality of the wire sheaths, each of the wire sheaths holding a portion of a corresponding one of the control wires.

14. An endoscope comprising:

a handle;

a flexible shaft connected to the handle, the shaft comprising a passive deflection section adjoining the handle and an active deflection section at a distal end, the passive deflection section encompassing wire sheaths therein; and means for controlling the deflection of the active deflection section comprising control wires connected to the active deflection section, a portion of each control wire passing through a corresponding one of the wire sheaths;

wherein each of the wire sheaths is an elongated solid tube which has a longitudinally constant cross-section and is made from super elastic alloy material, each of the wire sheaths being resiliently deflectable to bend with the passive deflection section and return to its original shape when released whereby permanent deformation or fatigue is minimized.

15. An endoscope as in claim 14 wherein each of the wire sheaths has an elongated generally cylindrical tubular shape.

16. An endoscope as in claim 14 wherein each of the wire sheaths has a substantially straight natural shape.

17. An endoscope as in claim 16 wherein each of the wire sheaths retains its natural shape so that when the passive deflection section is bent the wire sheaths assist the passive section return to a predetermined position.

* * * * *